United States Patent [19]
Davis et al.

[11] Patent Number: 6,123,717
[45] Date of Patent: *Sep. 26, 2000

[54] DISPOSABLE THERMAL NECK WRAP

[75] Inventors: Leane Kristine Davis, Milford; Ronald Dean Cramer; William Robert Ouellette, both of Cincinnati, all of Ohio; Dawn Michele Kimble, Reisterstown, Md.; Sandra Hintz Clear, Longwood, Fla.; Amy Michelle Martini, Cincinnati, Ohio

[73] Assignee: The Procter & Gamble Company, Cincinnati, Ohio

[ * ] Notice: This patent is subject to a terminal disclaimer.

[21] Appl. No.: 09/082,347

[22] Filed: May 20, 1998

Related U.S. Application Data

[63] Continuation-in-part of application No. 08/984,405, Dec. 3, 1997, abandoned, which is a continuation-in-part of application No. 08/777,642, Dec. 31, 1996, abandoned.

[51] Int. Cl.$^7$ ........................................ A61F 7/00
[52] U.S. Cl. .......................... 607/109; 607/114; 607/112
[58] Field of Search ........................ 607/104, 108–112, 607/114; 165/46; 126/204; 602/2

[56] References Cited

U.S. PATENT DOCUMENTS

| | | | |
|---|---|---|---|
| Re. 32,026 | 11/1985 | Yamashita et al. | 126/263 |
| 1,491,539 | 4/1924 | Kirschmann . | |
| 2,547,886 | 4/1951 | Poux | 62/1 |
| 2,562,121 | 7/1951 | Poux | 150/2.2 |
| 2,602,302 | 7/1952 | Poux | 62/1 |
| 3,463,161 | 8/1969 | Andrassy | 128/402 |
| 3,900,035 | 8/1975 | Welch et al. | 128/402 |
| 4,034,747 | 7/1977 | Leroy | 128/68.1 |
| 4,095,583 | 6/1978 | Petersen et al. | 126/263 |
| 4,205,685 | 6/1980 | Yoshida et al. | 128/399 |
| 4,255,157 | 3/1981 | Yamaguchi et al. | 44/3 C |
| 4,268,272 | 5/1981 | Taura | 44/3 R |
| 4,282,005 | 8/1981 | Sato et al. | 44/3 R |
| 4,366,804 | 1/1983 | Abe | 126/263 |
| 4,462,224 | 7/1984 | Dunshee et al. | 62/530 |
| 4,470,417 | 9/1984 | Gruber | 128/402 |
| 4,516,564 | 5/1985 | Koiso et al. | 126/263 |
| 4,575,097 | 3/1986 | Brannigan et al. | 128/402 |

(List continued on next page.)

FOREIGN PATENT DOCUMENTS

| | | | |
|---|---|---|---|
| 0 014 300 A1 | 8/1980 | European Pat. Off. | A61F 7/00 |
| 0 370 600 A1 | 7/1989 | European Pat. Off. | F24J 1/00 |
| 160443 | 9/1983 | India | C09K 3/02 |
| 58-37075 | 3/1963 | Japan | C09K 5/00 |
| 56-145846 | 11/1981 | Japan | A61F 7/03 |
| 57-170252 | 10/1982 | Japan | A61F 7/03 |
| 3-100090 | 4/1991 | Japan | C09K 5/00 |
| 5-317188 | 12/1993 | Japan | A47J 36/28 |
| 6-1969 | 1/1994 | Japan | C09K 5/00 |
| 6-315498 | 11/1994 | Japan | A61F 7/08 |
| 6-343658 | 12/1994 | Japan | A61F 7/08 |
| 7-67907 | 3/1995 | Japan | A61F 7/08 |
| 7-124192 | 5/1995 | Japan | A61F 7/08 |
| 7-49042 | 5/1995 | Japan | A61F 7/08 |
| 7-194641 | 8/1995 | Japan | A61F 7/08 |
| 7-194642 | 8/1995 | Japan | A61F 7/08 |
| 8-98856 | 4/1996 | Japan | A61F 7/08 |
| 8-126656 | 5/1996 | Japan | A61F 7/08 |
| 2 205 496 | 12/1988 | United Kingdom | A61F 7/03 |
| WO 94/00087 | 1/1994 | WIPO | A61F 7/00 |

*Primary Examiner*—Cary O'Connor
*Assistant Examiner*—Ryan Carter
*Attorney, Agent, or Firm*—Loy M. White; T. David Reed; David L. Suter

[57] ABSTRACT

The present invention relates to disposable thermal neck wraps having one or more thermal packs comprising a unified structure having at least one continuous layer of semirigid material, which has different stiffness characteristics over a range of temperatures, and a plurality of heat cells, wherein the heat energy is applied to specific areas of the upper back, neck and shoulders. More particularly, the present invention relates to disposable thermal neck wraps having good conformity to user's upper back, neck, and shoulders which provides consistent, convenient, and comfortable heat application.

50 Claims, 4 Drawing Sheets

U.S. PATENT DOCUMENTS

| | | | |
|---|---|---|---|
| 4,649,895 | 3/1987 | Yasuki et al. | 126/263 |
| 4,753,241 | 6/1988 | Brannigan et al. | 128/380 |
| 4,756,299 | 7/1988 | Podella | 126/263 |
| 4,805,620 | 2/1989 | Meistrell | 128/402 |
| 4,860,748 | 8/1989 | Chiurco et al. | 128/399 |
| 4,886,063 | 12/1989 | Crews | 128/403 |
| 4,891,501 | 1/1990 | Lipton | 219/527 |
| 4,925,743 | 5/1990 | Ikeda et al. | 428/702 |
| 4,981,135 | 1/1991 | Hardy | 128/402 |
| 5,025,777 | 6/1991 | Hardwick | 126/263 |
| 5,027,801 | 7/1991 | Grim | 128/80 H |
| 5,046,479 | 9/1991 | Usui | 126/204 |
| 5,072,598 | 12/1991 | Dibrell | 62/259.3 |
| 5,125,392 | 6/1992 | Hardwick | 126/263 |
| 5,148,804 | 9/1992 | Hill et al. | 128/402 |
| 5,211,949 | 5/1993 | Salyer | 424/402 |
| 5,233,981 | 8/1993 | Miyashita | 607/114 |
| 5,247,928 | 9/1993 | Stilts, Jr. | 607/109 |
| 5,342,412 | 8/1994 | Ueki | 607/114 |
| 5,366,492 | 11/1994 | Ueki | 607/114 |
| 5,395,399 | 3/1995 | Rosenwald | 107/108 |
| 5,405,671 | 4/1995 | Kamin et al. | 428/69 |
| 5,496,357 | 3/1996 | Jensen et al. | 607/108 |
| 5,496,358 | 3/1996 | Rosenwald | 607/108 |
| 5,507,793 | 4/1996 | Hodges | 607/109 |
| 5,605,144 | 2/1997 | Simmons et al. | 126/204 |
| 5,728,146 | 3/1998 | Burkett et al. | 607/109 |

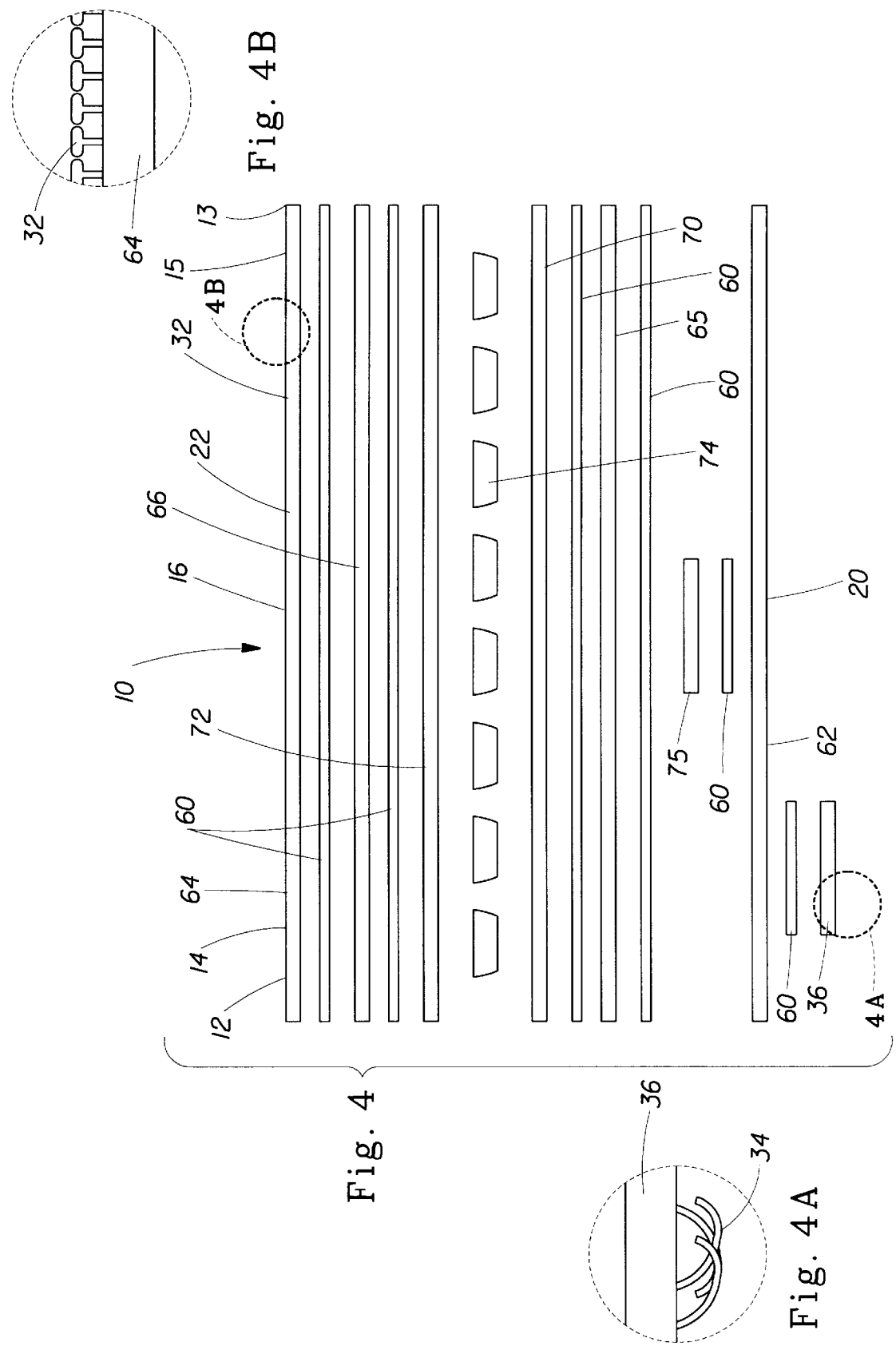

DISPOSABLE THERMAL NECK WRAP

CROSS REFERENCE TO RELATED APPLICATION

This application is a continuation-in-part of application Ser. No. 08/984,405, filed Dec. 3, 1997, now abandoned, which is a continuation-in-part of application Ser. No. 08/777,642, filed Dec. 31, 1996, now abandoned.

TECHNICAL FIELD

The present invention relates to disposable thermal neck wraps having one or more thermal packs comprising a plurality of individual heat cells, wherein the heat energy is applied to specific areas of the user's upper back, neck, and/or shoulders. More particularly, the present invention relates to disposable thermal neck wraps having good conformity to user's upper back, neck, and shoulders which provide consistent, convenient, and comfortable heat application.

BACKGROUND OF THE INVENTION

A common method of treating acute, recurrent, and/or chronic pain is by the topical application of heat to the afflicted area. Such heat treatments are used as a means of therapy for conditions which include aches, stiffness in muscles and joints, nerve pain, rheumatism and the like. Typically, the method for relieving pain using heat treatments has been to topically apply a relatively high heat, i. e., greater than about 40° C., for a short period of time, i. e., from about twenty minutes to about one hour.

Upper back, neck, and shoulder pain is generally associated with stress, bursitis, and upper back and neck muscular problems. Heating pads, hot water bottles, hot packs, hot towels, whirlpools, and hydrocollators have been commonly used to relieve the pain caused by such problems. Many of these devices employ reusable thermal packs containing, e.g., water and/or microwaveable gels. In general, most of these devices are inconvenient to use. Further, many of these thermal units or devices do not provide long lasting heat and also do not maintain a consistent temperature over long periods of time. The beneficial therapeutic effects from this administration of heat diminish after the heat source is removed.

The present inventors, however, have discovered that maintaining a sustained skin temperature of from about 32° C. to about 50° C., preferably from about 32° C. to about 45° C., more preferably from about 32° C. to about 42° C., most preferably from about 32° C. to about 39° C., still most preferably from about 32° C. to about 37° C., for a period of from about twenty seconds to about twenty-four hours, preferably from about twenty minutes to about twenty hours, more preferably from about four hours to about sixteen hours, most preferably from about eight hours to about twelve hours, wherein the maximum skin temperature and the length of time of maintaining the skin temperature at the maximum skin temperature may be appropriately selected by a person needing such treatment, such that the desired therapeutic benefits are achieved without any adverse events, such as skin burns which may be incurred by using a high temperature for a long period of time, substantially relieves acute, recurrent, and/or chronic upper back, neck, and/or shoulder pain, including skeletal, muscular, and/or referred upper back, neck, and/or shoulder pain, of a person having such pain.

The present inventors have further discovered that preferably maintaining a sustained skin temperature of from about 32° C. to about 43° C., preferably from about 32° C. to about 42° C., more preferably from about 32° C. to about 41° C., most preferably from about 32° C. to about 39° C., still most preferably from about 32° C. to about 37° C., for a time period of greater than about 1 hour, preferably greater than about 4 hours, more preferably greater than about 8 hours, even more preferably greater than about 16 hours, most preferably about 24 hours, substantially relieves acute, recurrent, and/or chronic upper back, neck, and/or shoulder pain, including skeletal, muscular, and/or referred upper back, neck, and/or shoulder pain, of a person having such pain and substantially prolongs relief even after the heat source is removed from upper back, neck, and/or shoulder.

Disposable heat packs based on iron oxidation, such as those described in U.S. Pat. Nos. 4,366,804, 4,649,895, 5,046,479 and Re. 32,026, are known. However, such devices have proven not totally satisfactory because many of these devices are bulky, cannot maintain a consistent and controlled temperature, have difficulty staying in place during use, and/or have unsatisfactory physical dimensions which hinder their effectiveness. Specifically, such devices cannot be easily incorporated into wraps which can comfortably conform to various body contours, and hence, they deliver short duration, inconsistent, inconvenient and/or uncomfortable heat application to the body.

The present inventors have developed disposable thermal neck wraps comprising one or more thermal packs having a unified structure, wherein each thermal pack comprises at least one continuous layer, preferably of a semirigid material, which is semirigid in specific areas of the thermal pack, yet which softens in between such areas when heated during use, most preferably comprising a coextruded material of polypropylene and ethylene vinyl acetate (EVA). The thermal pack or packs also comprises a plurality of individual heat cells, which typically comprise an exothermic composition, preferably comprising a specific iron oxidation chemistry, and having specific physical dimensions and fill characteristics, spaced apart and fixed within or to the unified structure of the thermal pack. Active heat cells, that is, heat cells having a temperature of about 35° C. or greater, soften narrow portions of the continuous layer or layers of semirigid material immediately surrounding the heat cells. Any remaining portions of the continuous layer or layers which surround the softened portions preferably remain more rigid. The narrow, softened portions act as hinges between the heat cells and between any remaining, cooler, more rigid portions, bending preferentially more than either the heat cells or more rigid portions. This results in thermal packs which possess sufficient rigidity to maintain structural support of the heat cells, to prevent unacceptable stretching of structures of the continuous layer or layers during processing or use, and to deter easy access to heat cell contents, while still maintaining good overall drape characteristics when heated. The thermal packs, when incorporated into the neck wraps of the present invention, provide efficient and effective heat coverage by having excellent conformity with the user's upper back, neck, and shoulders. These wraps also comprise alignment and position maintenance features.

The present inventors have also discovered that it may be desirable to selectively place heat cells, in the thermal pack or packs when incorporated into the neck wraps of the present invention, into positions fixed within or to the unified structure of the thermal pack, relative to each other which are sufficiently close so as to block some or all possible axes, which otherwise would have passed uninterrupted between the heat cells, through the thermal pack, or select regions thereof, to minimize or eliminate undesirable, uninterrupted fold lines, and/or to increase the structural support that the heat cell matrix imparts to the thermal pack. That is, placement of the heat cells into positions relative to each other which are sufficiently close to block some or all possible axes which would otherwise have passed uninterrupted, between the heat cells, causes the thermal packs to fold along a multiplicity of short interconnected fold lines oriented in a number of different directions relative to each other. Folding along a multiplicity of interconnected fold lines results in good overall drape characteristics.

It is therefore an object of the present invention to provide disposable thermal neck wraps which comprise one or more thermal packs, comprising a unified structure having at least one continuous layer, preferably of a semirigid material which has different stiffness characteristics over a range of temperatures, and a plurality of individual heat cells, which provide a controlled and sustained temperature and which reach their operating temperature range relatively quickly. The heat cells are spaced apart and fixed within or to the unified structure of the thermal pack.

It is also an object of the present invention to provide disposable thermal neck wraps which have good overall drapability while maintaining sufficient rigidity to maintain structural support of the heat cells, to prevent unacceptable stretching of the continuous layer or layers during processing or use, and/or to deter easy access to heat cell contents.

It is a further object of the present invention to provide disposable thermal neck wraps which can be worn under outer clothing with minimal visibility, which have alignment and position maintenance features, and which have a thermal element pattern that directs thermal energy to where it has the most therapeutic benefit.

It is a still further object of the present invention to provide methods of treating acute, recurrent, and/or chronic upper back, neck, and/or shoulder pain, including skeletal, muscular, and/or referred upper back, neck, and/or shoulder pain, of a person suffering from such pain, by maintaining a sustained skin temperature of from about 32° C. to about 50° C. for a period of time of from about twenty seconds to about twenty-four hours, preferably by maintaining a skin temperature of from about 32° C. to about 43° C. for a time period of greater than about 1 hour to provide prolonged relief from such pain.

These objectives and additional objectives will become readily apparent from the detailed description which follows.

SUMMARY OF THE INVENTION

The disposable thermal neck wraps of the present invention comprise at least one substantially U-shaped piece of flexible material having a first arm portion, a second arm portion, a central body portion therebetween, a body-facing surface, and an opposing outer surface, such that when the neck wrap is placed on a user, the central body portion is centered at the user's upper back and lower neck. First and second arm portions lay over the user's shoulders toward the user's chest.

The disposable thermal neck wraps of the present invention further comprise one or more thermal packs. The thermal packs comprise a unified structure having at least one continuous layer of a material which is preferably semirigid at a temperature of about 25° C., having a tensile strength of about 0.7 g/mm$^2$ or greater, and at least two-dimensional drape, and which is substantially less rigid at a temperature of 35° C. or greater, having a tensile strength substantially less than the tensile strength of the material at about 25° C.

The continuous layer or layers of the present invention preferably comprise a coextruded material, more preferably a coextruded material comprising polypropylene, most preferably a coextruded material wherein a first side comprises polypropylene and a second side comprises a tie-layer of a low melt temperature copolymer, preferably EVA.

The thermal pack(s) further comprises a plurality of individual heat cells, preferably comprising a mixture of powdered iron, powdered carbon, water, and salt, which when exposed to oxygen, provides a controlled and sustained temperature and which reach their operating temperature range quickly. The heat cells are spaced apart and fixed within or to the unified structure of the thermal pack. Preferably the heat cells are placed into positions fixed within or to the unified structure of the thermal pack, relative to each other and sufficiently close so that some or all of the possible axes that would otherwise pass uninterrupted between the heat cells are blocked by the heat cells to cause the thermal packs to fold along a multiplicity of short interconnected fold lines.

Preferably, the disposable thermal neck wraps of the present invention further comprise one or more attachment and/or positioning means fixedly attached to one or both distal ends of first and second arm portions, which serves to maintain the positioning of the thermal neck wrap during use by the wearer.

The present invention still further comprises methods of treating acute, recurrent, and/or chronic upper back, neck, and/or shoulder pain, including skeletal, muscular, and/or referred upper back, neck, and/or shoulder pain, of a person having such pain, by applying the disposable thermal neck wraps of the present invention to the upper back, neck, and/or shoulder of a person having such pain, to maintain a sustained skin temperature of from about 32° C. to about 50° C. for a period of time of from about twenty seconds to about twenty-four hours, preferably to maintain a skin temperature of from about 32° C. to about 43° C. for a time period of greater than about 1 hour, to provide prolonged relief from such pain.

All percentages and ratios used herein are by weight of the total composition, and all measurements made at 25° C., unless otherwise specified.

BRIEF DESCRIPTION OF THE DRAWINGS

While the specification concludes with claims which particularly point out and distinctly claim the present invention, it is believed that the present invention will be better understood from the following description of preferred embodiments, taken in conjunction with the accompanying drawings, in which like reference numerals identify identical elements and wherein:

FIG. 4 is a sectioned elevation view of FIG. 3, showing the laminate structure of the thermal neck wrap.

DETAILED DESCRIPTION OF THE INVENTION

Figure 1:
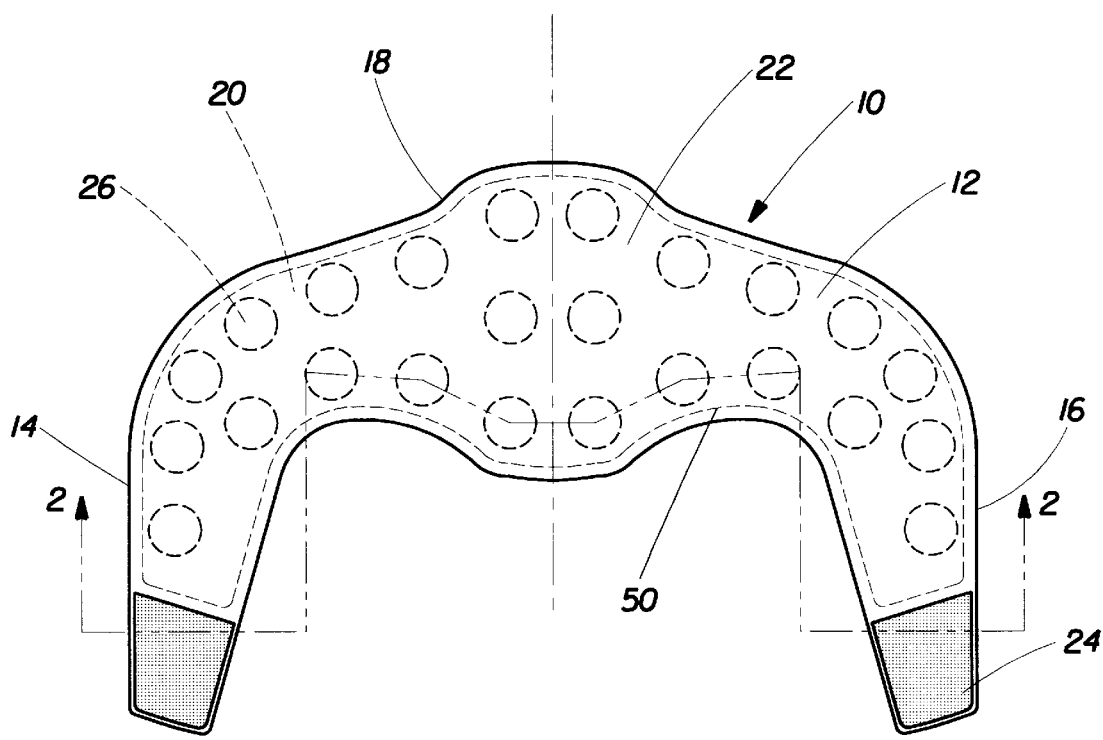
FIG. 1 is a top plan view of a preferred embodiment of the disposable thermal neck wrap of the present invention, showing a preferred pattern of thermal packs and/or heat cells.
Figure 2:
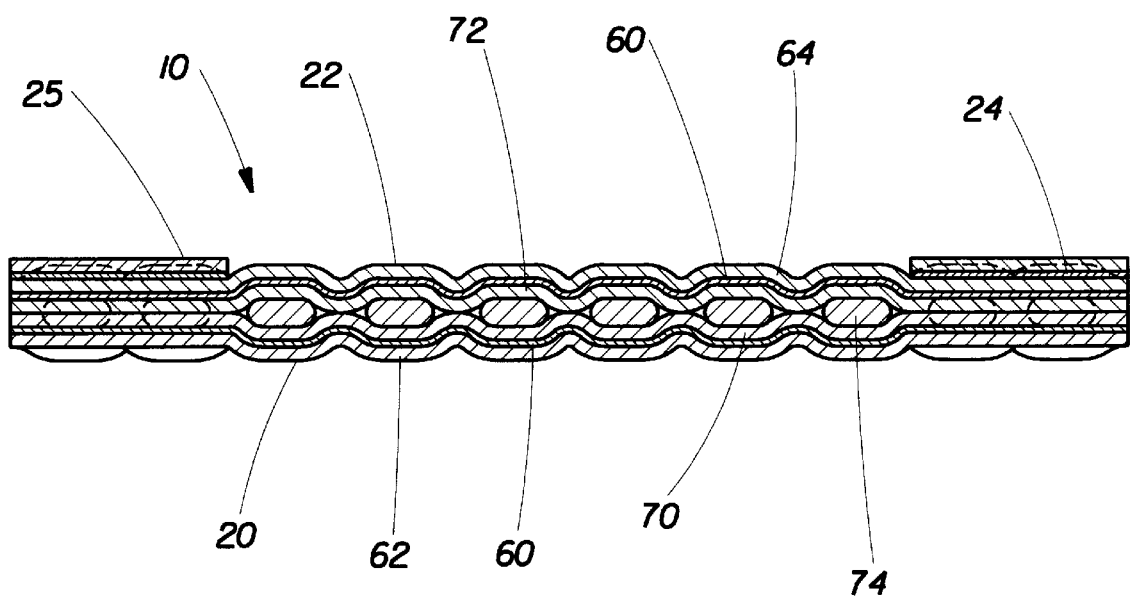
FIG. 2 is a sectioned elevation view of FIG. 1, showing the laminate structure of the thermal neck wrap.

The disposable thermal neck wraps of the present invention comprise one or more thermal packs having at least one continuous layer of a material which exhibits specific thermophysical properties, and a plurality of individual heat cells which preferably comprise an exothermic composition, spaced apart and fixed within or to the structure of the disposable thermal pack. The material of the at least one continuous layer is preferably semirigid when at room temperature, i.e., about 25° C., or below, but softens and becomes substantially less rigid when heated to about 35° C., or greater. Therefore, when heat cells, which are fixed within or to the unified structure of the thermal packs, are active, that is at a heat cell temperature of about 35° C. or greater, the narrow portion of the continuous layer or layers of material immediately surrounding each heat cell preferably softens and acts as a hinge between the heat cells and between any remaining, more rigid portions of the continuous layer or layers, bending preferentially more than either the heat cells or any cooler, more rigid portions. This results in thermal packs which possess sufficient rigidity to maintain structural support of the heat cells and prevent unacceptable stretching of structures of the continuous layer or layers during processing or use, while still maintaining good overall drape characteristics when heated. The disposable thermal neck wraps of the present invention provide consistent, convenient, and comfortable heat application, and an excellent conformity with user's upper back and the back portion of the user's neck, while retaining sufficient rigidity to deter easy access to heat cell contents.

"Disposable", as used herein, means that, while the thermal neck wraps of the present invention may be stored in a resealable, substantially air-impermeable container and reapplied to the user's body as often as required for the relief of pain, they are intended to be thrown away, i.e., deposited in a suitable trash receptacle, after the heat source, i.e., the heat cell(s) or thermal pack(s), has been fully expended.

"Heat cells", as used herein, means a unified structure, comprising an exothermic composition, preferably a specific iron oxidation chemistry, enclosed within two layers, wherein at least one layer may be oxygen permeable, capable of providing long lasting heat generation with improved temperature control, and having specific physical dimensions and fill characteristics. These heat cells can be used as individual heating units, or in a thermal pack comprising a plurality of individual heat cells which can also be easily incorporated into disposable body wraps, pads, and the like. Thermal packs and body wraps incorporating thermal packs adapt to a wide variety of body contours, thus providing consistent, convenient, and comfortable heat application.

"Plurality of heat cells", as used herein, means more than one, preferably more than two, more preferably more than three, most preferably more than four, heat cells.

"Agglomerated pre-compaction composition", as used herein, means the mixture of dry powdered ingredients, comprising iron powder, carbonaceous powder, metal salt(s), water-holding agent(s), agglomeration aid(s), and dry binder(s) prior to direct compaction.

"Direct compaction", as used herein, means a dry powder mixture is blended, compressed, and formed into pellets, tablets, or slugs without the use of typical wet binders/solutions to adhere the particulate(s) together. Alternatively, the dry powder mixture is blended and roll compacted or slugged, followed by milling and screening, creating directly compacted granules. Direct compaction may also be known as dry compaction.

"Heating element(s)", as used herein, means the exothermic, direct compacted, dry agglomerated pre-compaction composition formed into compaction articles, such as granules, pellets, slugs, and/or tablets capable of generating heat, after an aqueous solution such as water or brine (salt solution) is added, by the exothermic oxidation reaction of iron. Agglomeration granules of said agglomerated pre-compaction composition are also included as heating elements herein.

The "fill volume", as used herein, means the volume of the particulate composition or the compacted, water-swelled, heating element in the filled heat cell. The "void volume", as used herein, means the volume of the cell left unfilled by the particulate composition or the compacted, water-swelled, heating element in a finished heat cell, not including the unfilled space within a tablet comprising a hole or reservoir, in a finished heat cell, measured without differential pressure in the heat cell and without additional stretching or deformation of the substrate material. The "cell volume", as used herein, means the fill volume plus the void volume of the heat cell.

"Continuous layer or layers", as used herein, means one or more layers of a material which may be uninterrupted or partially, but not completely, interrupted by another material, holes, perforations, and the like, across its length and/or width.

"Rigid", as used herein, means the property of a material wherein the material may be flexible, yet is substantially stiff and unyielding, and which does not form fold lines in response to gravitational pull or other modest forces.

"Semirigid material", as used herein, means a material which is rigid to some degree or in some parts, i. e., having at least two-dimensional drape at a temperature of about 25° C., and exhibits a toughness to maintain structural support of the heat cells in an unsupported format, and/or prevent unacceptable stretching of structures of the material during processing or use, while still maintaining good overall drape characteristics when heated, and/or retaining sufficient rigidity to deter easy access to heat cell contents.

"Two dimensional drape", as used herein, means drape which occurs across a continuous layer or layers, across a thermal pack, or across a select region of a layer or layers, or thermal pack, exclusively along one axis, i.e., one fold line forms, at the expense of other axes in response to gravitational pull or other modest forces.

"Three dimensional drape", as used herein, means drape which simultaneously occurs across a continuous layer or layers, across a thermal pack, or across a select region of a layer or layers, or thermal pack, along two or more axes, i. e., two or more fold lines form, in response to gravitational pull or other modest forces.

"Fold lines", as used herein, means the line along which a material forms a temporary or permanent crease, ridge, or crest in response to gravitational pull or other modest forces.

It is understood that the disposable thermal neck wraps of the present invention may comprise one or more thermal packs. However, for clarity a disposable thermal neck wrap comprising a single thermal pack will be described herein.

Referring now to the drawings, there are shown preferred embodiments of the present invention, which provide a disposable thermal neck wrap, generally indicated as 10. Thermal neck wrap 10 comprises a unitary structure having at least one piece of flexible material 11, which comprises a first arm portion 14 comprising a first end 12, a second arm portion 15 comprising a second end 13, and a central body portion 16 therebetween. The at least one piece of flexible material 11 further comprises a first edge 17 and an opposing second edge 18, both of which extend continuously from first end 12 to second end 13. First edge 17 has a length less than the length of opposing second edge 18, providing thermal neck wrap 10 a substantially U-shaped configuration, such that first edge 17 defines a substantially circular interior arc and second edge 18 defines a substantially circular exterior arc of thermal neck wrap 10. When neck wrap 10 is worn, first and second arm portions 14 and 15 extend over the shoulders of the wearer toward the upper chest. Central body portion 16 is located on the user's upper back and the back portion of the user's neck.

Figure 3:
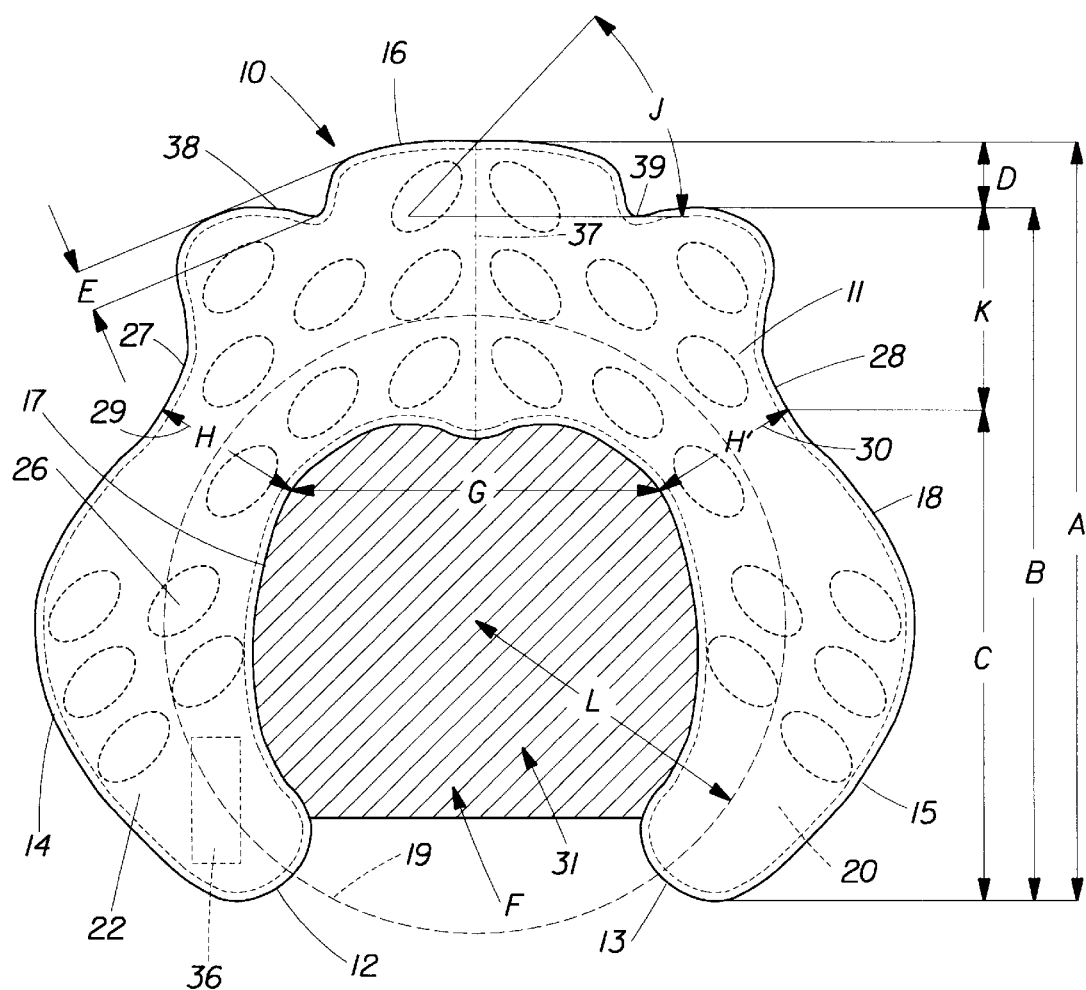
FIG. 3 is a top plan view of another preferred embodiment of the disposable thermal neck wrap of the present invention, showing a preferred pattern of heat cells and shape of the thermal neck wrap.

Several elements of neck wrap 10, as shown in FIGS. 1–4, allow neck wrap 10 to easily move with the movement of the user's body to provide broad coverage of the neck, upper back, and shoulders, for consistent, convenient, and comfortable heat application, and excellent conformity with user's neck, upper back, and shoulders. More specifically, neck wrap 10 fits around the user's neck substantially without the sensation of choking the user. Further, neck wrap 10 self aligns to the user's shoulders during placement and wear, and drapes and conforms to the user's upper back, shoulders, and upper chest area, minimizing interference with the user's body movement. As shown in FIG. 3, these benefits are achieved by the neck/shoulder junction 19 of neck wrap 10 having a radius L of from about 120 mm (4.7 inches) to about 190 mm (7.5 inches), preferably from about 130 mm (5.1 inches) to about 180 mm (7.1 inches), more preferably from about 140 mm (5.5 inches) to about 170 mm (6.7 inches), most preferably from about 150 mm (5.9 inches) to about 160 mm (6.3 inches). Another way these benefits are achieved is the width H at the first arm portion/central body portion junction 29 and width H' at the second arm portion/central body portion junction 30 of neck wrap 10. Widths H and H' of neck wrap 10 at junction 29 and 30 are preferably, but not limited to, equal measure and may be made longer or shorter, as appropriate, by varying the depth of first and second concave cut-outs 27 and 28 in second edge 18 at the first arm portion/central body portion junction 29 and second arm portion/central body portion junction 30. Concave cut-outs 27 and 28 are placed over the shoulders of the user during wear and allow neck wrap 10 to self align to the user's shoulders during initial placement and wear. That is, a force acting on neck wrap 10 that would otherwise impart a slight spinning motion to neck wrap 10 around the user's neck is opposed by a resisting force as the second edge 18 of wrap 10 at concave cut-outs 27 and 28 cuts in (not into) against the user's shoulders. Similarly, if neck wrap 10 is lifted out of place during wear and replaced slightly out of position, second edge 18 at concave cut-outs 27 and 28 cuts in against the user's shoulders, creating a force that overcomes the frictional force of neck wrap 10 against the user's body. This imparts a slight spinning motion around the neck that moves neck wrap 10 back into position, at which point the force is relieved. There are no heat cells 26 over the top of user's shoulders to maximize contact between neck wrap 10 and the user's body, over the shoulders, enabling the first set of heat cells 26 in front of, and separately, in back of user's shoulders to press against user's shoulders when neck wrap 10 is in position, augmenting the action of concave cut-outs 27 and 28.

Width H and/or H' of neck wrap 10 at junction 29 and 30 is preferably from about 45 mm (1.8 inch) to about 100 mm (4 inches) more preferably from about 55 mm (2.2 inches) to about 90 mm (3.5 inches), most preferably from about 65 mm (2.6 inches) to about 80 mm (3.1 inches). It is further preferred that the sum of width H of first arm portion/central body portion junction 29, and width H' of second arm portion/central body portion junction 30, and the width G of neck aperture 31 at junction 29 and 30, is from about 270 mm (10.6 inches) to about 400 mm (15.7 inches) more preferably from about 295 mm (11.6 inches) to about 365 mm (14.4 inches), most preferably from about 320 mm (12.6 inches) to about 340 mm (13.4 inches). More preferably, the ratio of width H and/or H' of neck wrap 10 at junction 29 and 30 to width G of neck aperture 31 is preferably in the range of from about 1:2 to about 1:4, more preferably from about 1:2 to about 1:3, most preferably from about 1:2.3 to about 1:2.5.

First shoulder blade notch 38 and second shoulder blade notch 39 are positioned along second edge 18, between first arm portion/central body portion junction 29 and center line 37 of central body portion 16, and between second arm portion/central body portion junction 30 and center line 37 of central body portion 16. Center line 37 preferably approximately bisects central body portion 16, substantially perpendicular to first edge 17 and second edge 18. Shoulder blade notches 38 and 39 are preferably substantially triangular shaped having a height E (apex) and a width D (base) such that the ratio of E:D is less than or equal to about 1:3, preferably less than or equal to about 1:2, more preferably less than or equal to about 1:1.5, most preferably about 1:1.4.

To provide further preferred drape and conformity to the neck, upper back, and shoulders of the user, elliptical shaped heat cells 26 are, preferably positioned within thermal pack 50, such that heat cells 26 are oriented relative to center line 37 of central body portion 16 at angle J, which allows the major axis of each elliptical heat cell 26 to run with, rather than against, the user's body's natural contour lines. In this way, when neck wrap 10 hinges around each elliptical heat cell 26, most of the hinging occurs in a direction substantially parallel to the major axis of elliptical heat cell 26 more than in a direction substantially parallel to the minor axis of elliptical heat cell 26. The elliptical heat cells 26 are preferably positioned such that the major axis each diagonal grouping of elliptical heat cells 26 work together, such that the overall drape of neck wrap 10 follows the natural contour lines of the user's body. That is, the combined hinging approximates the contour lines of the user's body. Preferably angle J of elliptical heat cells 26 is from about 20 degrees to about 70 degrees, more preferably from about 30 degrees to about 60 degrees, most preferably from about 35 degrees to about 50 degrees.

The preferred neck wrap 10, shown in FIG. 3, has further preferred elements and/or dimensions which provide and/or contribute to the preferred drape and conformity of neck wrap 10 to the user's neck, upper back, and shoulders. That is, the ratio of the length C of first arm portion 14 and/or second arm portion 15 to overall length A of neck wrap 10 (i. e., C:A) is preferably from about 1:1 to about 1:2, more preferably from about 1:1.4 to about 1:1.85, most preferably from about 1:1.5 to about 1:1.7. Further, the ratio of length C of first arm portion 14 and/or second arm portion 15 to area F of neck aperture 31 (i. e., C:F) is preferably from about 1 (mm):125 (mm$^2$) to about 1 (mm):190 (mm$^2$), more preferably from about 1 (mm):135 (mm$^2$) to about 1 (mm):180 (mm$^2$), most preferably from about 1 (mm):150 (mm$^2$) to about 1 (mm):170 (mm$^2$).

Wrap 10 has a body-facing surface 20, comprising body-facing material 62 and an opposing outer surface 22, comprising outer surface material 64. Body-facing material 62 and outer surface material 64 may be selected from any number of suitable materials including, but not limited to, wovens, knits, films, foams and nonwovens including spunbond, carded, meltblown, hydroentangled, through-air bonded, air laid, and wet laid. These materials may be made from natural fibers including, but not limited to, cotton, wool, linen, or manmade polymeric materials such as polypropylene, polyester, nylon, polyethylene, metallocene catalyst polyethylene, and the like.

A material that has been found to be suitable for body-facing material 62 and/or outer surface material 64 is a carded thermally bonded nonwoven of polypropylene with a basis weight of about 65 g/m² (54 grams per square yard (gsy)). This material is available as grade #9354990 from Veratec, Walpole, Mass.

A preferred material suitable for body-facing material 62 and/or outer surface material 64 is a carded thermally bonded nonwoven of polypropylene with a basis weight of about 32 g/m² (27 gsy). This material is available as grade #9327786 from Veratec, Walpole, Mass.

Preferably, neck wrap 10 further comprises at least one carrier layer 65, interposed between body-facing material 62 and outer surface material 64, or between body-facing material 62 and thermal pack 50, and/or at least one bulking layer 66, interposed between body-facing material 62 and outer surface material 64, or between outer surface material 64 and thermal pack 50. Carrier layer 65 and/or bulking layer 66 may be made of the same materials as those described for body-facing material 62 and/or outer surface material 64. Preferably, carrier layer 65 include, but are not limited to, wovens, knits, films, foams and nonwovens including spunbond, carded, meltblown, hydroentangled, through-air bonded, air laid, and wet laid. These materials may be made from natural fibers including, but not limited to, cotton, wool, linen, or manmade polymeric materials such as polyethylene, polypropylene, nylon, polyester, polyvinyl chloride, polyvinylidene chloride, polyurethane, polystyrene, saponified ethylene-vinyl acetate copolymer, ethylene-vinyl acetate copolymer, natural rubber, reclaimed rubber, synthetic rubber, and mixtures thereof. These materials may be used alone, extruded, coextruded, or coextruded with a low melt temperature polymer including, but not limited to, ethylene vinyl acetate copolymer, low density polyethylene, and mixtures thereof. Preferably, bulking layer 66 may be any number of different materials including, but not limited to, wovens, knits, carded nonwovens, spunbond nonwovens, combinations of these materials, and the like. These fabrics may be made of either natural or synthetic fibers including, but not limited to, polypropylene, polyethylene, polyester, nylon, rayon, cotton, cellulose, and the like. A material that has been successfully used for carrier layer 65 and/or bulking layer 66, is a 32 g/m² (27 gsy) thermally bonded carded polypropylene nonwoven available as grade #9327786 from Veratec, Walpole, Mass. Another material which has been used successfully for carrier layer 65 and/or bulking layer 66 is a spunbond/meltblown/spunbond (SMS) laminate available as Ultramesh Grade #L4990.4, from Veratec, Walpole, Mass.

It is preferred, that neck wrap 10 have a lightness measurement (L*) on outer surface 22 over heat cell(s) of at least about 5 units greater than the lightness measurement on body-facing surface 20 over heat cell(s) 26, to provide a contrast between the body side (inside of thermal neck wrap 10) and clothing side (outside of thermal neck wrap 10), making thermal neck wrap 10 easier/more intuitive to the user to put on. An L* value of not less than about 65 and not greater than about 80 on the body-facing surface 20, and about 78 or greater on outer surface 22 is preferred. These L* values are/may be achieved by adjusting, as appropriate, the number of layers and/or thickness (basis weight) of outer surface material 64 and/or bulking layer 66 and/or carrier layer 65 and/or body-facing material 62 and/or base layer 70 and/or cover layer 72.

Lightness may be measured using any suitable method and/or instrument for measuring lightness/chromaticity. One method which has been found useful uses a Minolta Chroma Meter CR-300, manufactured by Minolta Camera Company, Ramsey, N.J., wherein neck wrap 10 is placed on a sheet of plain white paper and the measuring head placed on neck wrap 10 at the specific site to be measured. L* values are recorded (an average of three measurements) at sites between heat cells 26 and sites directly over heat cells 26, on both the body-facing surface 20 and outer surface 22. Methods, instrument information, and a definition of chromaticity may be found in the *Chroma Meter CR-300/CR-310/CR-321/CR-331/CR-331C Instruction Manual*, by The Minolta Camera Company, Ramsey, N.J., which is incorporated herein by reference in its entirety.

During use, thermal neck wrap 10 is draped over the shoulders of the wearer. Preferably, an attachment and/or positioning means, such as adhesive patches 24, are located toward the upper chest of the wearer and serve to maintain the positioning of thermal neck wrap 10. Preferably, one or more adhesive patches 24 are fixedly attached at or near one or both of the distal ends 12 and 13 of first and second arm portions 14 and 15.

Adhesive patches 24 are preferably fixedly attached to outer surface 22 of first and second arms 14 and/or 15 near their respective distal ends 12 and 13, beyond the location of heat cells 26 of the thermal pack(s) 50, which are designed to reside in front of the shoulders, and of the heat cells 26 of thermal pack(s) 50 of body portion 16, which are designed to reside behind the shoulders of the wearer.

Preferably, adhesive patches 24 may be pressure sensitive adhesive circles, squares, or other shapes.

Adhesive patches 24 are preferably protected prior to use by a removable release paper 25. Upon use, removable release paper 25 is removed exposing adhesive patches 24. Adhesive patches 24 may then be applied against the underside of the wearer's clothing, or adhesive patch 24 of first arm 14 may be applied to the body-facing surface 20 of second arm 15, or adhesive patch 24 of second arm 15 may be applied to the body-facing surface 20 of first arm 14.

Alternatively, adhesive patches 24 may be fixedly attached to body-facing-surface 20 of first arm 14 and/or second arm 15, and applied to the skin of the user, or adhesive patch 24 of first arm 14 may be applied to the outer surface 22 of second arm 15, or adhesive patch 24 of second arm 15 may be applied to the outer surface 22 of first arm 14.

Adhesive patches 24 may be any number of suitable adhesive materials which is capable of attaching to clothing and/or skin. A particularly suitable material that has been used successfully is positioning adhesive 34-5598 available from National Starch and Chemical Co., Bridgewater, N.J. Release paper 25 may be any suitable polymeric film or paper which has been designed or treated to release from the adhesive used for adhesive patches 24. BL 25 MGA SILOX C3R/0 available from Akrosil has been shown to be suitable for this purpose.

Alternatively, adhesive patches 24 may be preapplied to a substrate prior to assembly of wrap 10. The substrate is then attached to outer surface material 64 by a suitable means.

Other types of attachment and/or positioning means which may be useful in the present invention include, but are limited to, hook and loop fastening systems.

A more preferred attachment and/or positioning means comprises a hook and loop fastening system having hook member 36, comprising a plurality of hooks 34, preferably fixedly attached to body-facing surface 20 at or near at least one of first end 12 and second end 13. Hook member 36 may alternatively be fixedly attached to outer surface 22 at or near at least one of first end 12 and second end 13. Preferably, body-facing surface 20 and/or outer surface 22 comprise a plurality of loop fibers 32 disposed along the extent of first arm portion 14 and/or second arm portion 15 to form a continuous landing zone which serves as the loop member of the reclosable hook and loop fastening system.

Hooks 34 may be any number of styles, shapes, and/or densities depending upon the use. Hooks 34 may be bent shafts, mushroom capped, harpoon-shaped, or any other suitable shape. Hooks 34 may be unidirectional, bi-directional, or omni-directional depending upon the application and companion loop fibers 32. Hooks 34 must be chosen in conjunction with companion loop fibers 32 so as to provide the peel and shear forces that are required for different applications.

Hook member 36 and loop fibers 32 ideally are chosen to provide shear strength greater than the tension exerted by wrap 10 during use. Hook member 36, which has been found to work particularly well, comprises hooks 34 which are harpoon shaped and are available as KN-0561 from 3M, Minneapolis, Minn. Hook member 36 is permanently attached to neck wrap 10 by means of ultrasonic bonding, pressure bonding, adhesives, and/or stitching.

The materials from which the wrap are constructed must be selected such that once they are combined in the product the product must be adapted to both easily drape over and conform to the body curvature and to provide minimal translation of compressive force along and in the plane of the product. In the present invention the layers are combined with pressure sensitive hot melt glue layers 60. Glue layer 60 may be applied via a=approximately 0.31 system at a level of =approximately 0.31 to 2.5 mg/cm$^2$ (0.002 to 0.016 grams per square inch). A particularly suitable adhesive for glue layer 60 is pressure sensitive hot melt adhesive 70-4589 available from National Starch & Chemical Co., Bridgewater, N.J. Alternatively, combining or assembly means may include, but not limited to, thermal dot bonding, melt blown hot melt glue, bead applied hot melt glue, ultrasonic bonding, pressure bonding, and/or thermal bonding.

Thermal neck wrap 10 further comprises one or more thermal packs 50, preferably interposed and fixed within the unitary structure of neck wrap 10. Each thermal pack 50 comprises a plurality of individual heat cells 26, preferably spaced apart and fixed within the laminate structure of the thermal pack 50. Alternatively, each thermal pack 50 may comprise a single continuous base layer 70, wherein individual or groups of heat cells 26 are fixedly attached to and spaced apart across the base layer 70.

The heat cells 26 of thermal pack 50 can have any geometric shape, e.g., disk, triangle, pyramid, cone, sphere, square, cube, rectangle, rectangular parallelepiped, cylinder, ellipsoid and the like. The preferred shape of the heat cells 26 comprises an ellipsoid (i. e., oval), having a width at its widest point of from about 0.15 cm to about 20 cm, preferably from about 0.3 cm to about 10 cm, more preferably from about 0.5 cm to about 5 cm, most preferably from about 1 cm to about 3 cm, a height at its highest point of from greater than about 0.2 cm to about 5 cm, preferably from greater than about 0.2 cm to about 1 cm, more preferably from greater than about 0.2 cm to about 0.8 cm, and most preferably from about 0.3 cm to about 0.7 and a length at its longest point of from about 0.5 cm to about 20 cm, preferably from about 1 cm to about 15 cm, more preferably from about 1 cm to about 10 cm, most preferably from about 3 cm to about 5 cm. Alternatively, the heat cells may preferably comprise a disk shaped geometry having a cell diameter of from about 0.2 cm to about 10 cm, preferably from about 0.5 cm to about 8 cm, more preferably from about 1 cm to about 5 cm, and most preferably from about 1.5 cm to about 3 cm. The heat cells 26 have a height of from greater than about 0.2 cm to about 1 cm, preferably from greater than about 0.2 cm to about 0.9 cm, more preferably from greater than about 0.2 cm to about 0.8 cm, and most preferably from about 0.3 cm to about 0.7 cm.

Heat cells 26 are spaced apart from each other and each heat cell 26 functions independently of the rest of the heat cells 26. While the heat cells may comprise any suitable composition providing heat, such as exothermic compositions, microwaveable compositions, heat of crystallization compositions, and the like, the preferred heat cell contains a densely packed, particulate exothermic composition 74 which substantially fills the available cell volume within the cell reducing any excess void volume, thereby minimizing the ability of the particulate matter to shift within the cell. Alternatively, the exothermic composition 74 may be compressed into a hard tablet before being placed in each cell. Because the heat generating material is densely packed or compressed into a tablet, the heat cells 26 are not readily flexible. Therefore, the spacing apart of the cells and the materials selected for base layer 70 and/or cover layer 72 allows each thermal pack 50, and ultimately neck wrap 10, to easily conform to the user's upper back, neck, and shoulders.

Heat cells 26 are positioned within thermal pack 50 such that, when wrap 10 is properly positioned on the user, the heat cells 26 reside behind or on top of the user's shoulders, neck, and/or upper back to approximate the shape and location of muscles in the user's upper back, lower neck, and/or shoulders, to provide heat to said areas of user's body. Heat cells 26 located near first and second arms 14 and 15 are designed to reside in front of or on top of the user's shoulders to provide a means of counter-balancing the weight of the heat cells 26 located in central body portion 16. They may also provide heat to user's upper chest and/or front of user's shoulders and/or neck.

Base layer 70 and cover layer 72 are preferably continuous layers which may be made of any number of suitable materials. Preferably, base layer 70 and/or cover layer 72 comprise materials which are semirigid at a temperature of about 25° C. and which soften, i.e., becomes substantially less rigid, at a temperature of about 35° C., or greater. That is, the materials preferably have a tensile strength, within the elastic deformation range of the material, of about 0.7 g/mm$^2$ or greater, more preferably about 0.85 g/mm$^2$ or greater, most preferably about 1 g/mm$^2$ or greater, at about 25° C. and a tensile strength substantially less at about 35° C. or greater. "Substantially less", as used herein, means that the tensile strength of the material at about 35° C., or greater, is statistically significantly less than the tensile strength at about 25° C., at an appropriate statistical confidence (i. e., 95%) and power (i. e., ≧90%).

Therefore, when heat cells 26, which are fixed within or to the unified structure of thermal pack 50, are active, that is at a heat cell temperature of from about 35° C. to about 60° C., preferably from about 35° C. to about 50° C., more preferably from about 35° C. to about 45° C., and most preferably from about 35° C. to about 40° C, the narrow portion of the continuous layer or layers of material immediately surrounding each heat cell softens and acts as a hinge between the heat cells and between any remaining, cooler, more rigid portions of the continuous layer or layers, bending preferentially more than either the heat cells or more rigid portions. This results in thermal pack 50 which possess sufficient rigidity to maintain structural support of the heat cells and to prevent unacceptable stretching of structures of the continuous layer or layers during processing or use, while still maintaining good overall drape characteristics when heated. When thermal pack 50 of the present invention is incorporated into neck wrap 10, neck wrap 10 easily adapts to a wide variety of body contours, provides consistent, convenient, and comfortable heat application, and an excellent conformity with body forms, while retaining sufficient rigidity to prevent wrap 10 from folding or bunching during use and deter easy access to heat cell contents.

Typically, the tensile strength may be measured using a simple tensile test on an electronic tensile test apparatus, such as a universal constant rate elongation tensile testing machine with computer, Instron Engineering Corp., Canton, Mass. Any standard tensile test may be used, for example, material samples are cut into strips having a width of about 2.54 cm (about 1 inch) and a length of from about 7.5 cm to about 10 cm (about 3 to about 4 inches). The ends of the strips are placed into the jaws of the apparatus with enough tension to eliminate any slack, but without loading the load cell. The temperature of the sample is then allowed to stabilize at the desired test temperature. The load cell of the apparatus is set for about 22.7 kg (50 pound) load, the elongation set for 5 mm, and the crosshead speed is set for about 50 cm/min. The apparatus is started and the tensile strength data is collected by the computer. The sample is then removed from the apparatus.

The tensile strength is calculated as the slope of the tensile load vs. the extension during elastic deformation of the materials using the equation:

$$m = (L/E)$$

Where m=the slope in $g/mm^2$ during elastic deformation;

L=the load at extension in g/mm; and

E=the extension in mm.

Preferably, base layer 70 and/or cover layer 72 comprise at least two-dimensional drape at about 25° C., i. e., a single fold line occurs in the material along a single axis, and three-dimensional drape at about 35° C. or greater, i. e., two or more fold lines occur along multiple axes. Drape may be determined by placing and centering a square sample, for example about 30 cm by about 30 cm (about 12 inches by about 12 inches), of material on the end of a cylindrical shaft with a pointed end, allowing the material to drape due to gravitational forces, and the number of fold lines counted. Material that exhibit one-dimensional drape, i.e., have no fold lines in any direction, are determined to be rigid, while materials that exhibit at least two-dimensional drape, i.e., have at least one fold line forming along at least one axis, are determined to be semirigid.

Different materials may be capable of satisfying the specified requirement for base layer 70 and/or cover layer 72 provided that the thickness is adjusted accordingly. Such materials may include, but are not limited to, polyethylene, polypropylene, nylon, polyester, polyvinyl chloride, polyvinylidene chloride, polyurethane, polystyrene, saponified ethylene-vinyl acetate copolymer, ethylene-vinyl acetate copolymer, natural rubber, reclaimed rubber, synthetic rubber, and mixtures thereof These materials may be used alone, preferably extruded, more preferably coextruded, most preferably coextruded with a low melt temperature polymer including, but not limited to, ethylene vinyl acetate copolymer, low density polyethylene, and mixtures thereof Preferably, base layer 70 and cover layer 72 comprise polypropylene, more preferably a coextruded material comprising polypropylene, most preferably a coextruded material wherein a first side comprises polypropylene, preferably from about 10% to about 90%, more preferably from about 40% to about 60%, of the total thickness of the material, and a second side comprises a tie-layer of a low melt temperature copolymer, preferably EVA. Base layer 70 and/or cover layer 72 preferably have a basis weight thickness of less than or equal to about 100 μm, more preferably less than or equal to about 75 μm, most preferably less than or equal to about 50 μm.

More preferably, base layer 70 and/or cover layer 72 comprise a coextruded material, having a first side of polypropylene and a second side of EVA. Preferably cover layer 72 has a thickness of from about 20 μm to about 30 μm, more preferably about 25 μm, and base layer 70 has a thickness of from about 20 μm to about 30 μm, more preferably about 25 μm. Still more preferably, cover layer 72 has a thickness of from about 40 μm to about 60 μm, most preferably about 50 μm (2 mils), and base layer 70 has a thickness of from about 20 μm to about 30 μm, most preferably about 25 μm (1 mil), wherein the polypropylene comprises about 50% and the EVA tie-layer comprises about 50% of the total thickness of base layer 70 or cover layer 72. A particularly suitable material is available as P18-3161 from Clopay Plastics Products, Cincinnati, Ohio. The P18-3161 which is preferable for cover layer 72 has been subjected to a post process aperturing with hot needles to render it permeable to oxygen.

When coextruded materials of the type just described are used for base layer 70 and cover layer 72, the EVA sides are preferably oriented toward each other to facilitate thermal bonding of cover layer 72 to base layer 70.

Good overall drape characteristics and/or excellent conformity with user's upper back, neck, and/or shoulders, and/or increased structural support to the thermal pack 50, may also be achieved by selectively placing the heat cells 26 into positions fixed within or to the unified structure of the thermal pack 50 relative to each other which are sufficiently close so as to block some or all possible axes across the material of the continuous layer and/or layers 70 and/or 72, which otherwise would have passed uninterrupted between the heat cells 26, through the thermal pack 50, or select regions thereof, to minimize or eliminate undesirable, uninterrupted fold lines. That is, placement of the heat cells 26 into positions relative to each other which are sufficiently close so that the number of axes which pass uninterrupted, between the heat cells 26, is selectively controlled, such that the continuous base layer 70 and cover layer 72 of thermal pack 50, or select regions thereof, preferably folds along a multiplicity of short interconnected fold lines oriented in a number of different directions relative to each other. Folding along a multiplicity of interconnected fold lines results in thermal packs 50 which have good overall drape characteristics, readily conform with user's upper back, neck, and/or shoulders, and/or have increased structural support of the heat cell matrix.

Because heat cells 26 are not readily flexible, the spacing between heat cells 26 provides the preferred benefits and may be determined, when selectively placing heat cells 26 within or fixed to the unified structure of thermal packs 50, wherein at least one heat cell of four adjacent heat cells, whose centers form a quadrilateral pattern, blocks one or more axes that could otherwise form at least one fold line tangential to the edges of one or more pairings of the remaining three heat cells in the quadrilateral pattern. Preferably, elliptical heat cells 26 in central body portion 16, approximates the muscles in the upper back and/or shoulders, and are preferably spaced apart, such that a plurality of fold lines can form between elliptical heat cells 26, but not so far apart that elliptical heat cells 26 in the matrix stop working together to influence the overall drape of neck wrap 10. Spacing between elliptical heat cells 26 is preferably greater than the minimum s diameter of elliptical heat cells 26 divided by 2, multiplied by 0.75, but more preferably, not greater than the minimum diameter of elliptical heat cells 26.

$$((W/2)*0.75) \leq s \leq W$$

Where s=the closest distance between the heat cells; and

W=the measurement of the smallest diameter of the smallest diameter heat cell within the pattern.

Alternatively, the spacing between at least one heat cell of the four adjacent heat cells and each of the heat cells of the one or more pairings of the remaining heat cells in the quadrilateral pattern may be calculated using the equation:

$$s \leq (W_q/2)*0.75$$

Where s=the closest distance between the heat cells; and $W_q$=the measurement of the smallest diameter of the smallest diameter heat cell within the quadrilateral pattern.

In the further alternative, the spacing between heat cells 26 may be determined wherein, at least one heat cell of three adjacent heat cells, whose centers form a triangular pattern, blocks one or more axes that could otherwise form at least one fold line tangential to the edges of the remaining pair of heat cells in the triangular pattern formed by the three heat cells. Most preferably, the spacing between the at least one heat cell of the three adjacent heat cells and each heat cell of the remaining pair of heat cells in the triangular pattern may be calculated using the equation:

$$s \leq (W_t/2)*0.3$$

Where s=the closest distance between the heat cells; and $W_t$=the measurement of the smallest diameter of the smallest diameter heat cell within the triangular pattern.

Different materials may be capable of satisfying the above specified requirements for base layer 70 and/or cover layer 72. Such materials may include, but are not limited to, those materials mentioned above.

A most preferred embodiment of the disposable thermal packs 50 of the present invention comprises at least one continuous layer of semirigid material having the thermophysical properties described above, and the heat cells 26 fixed within or to the unified structure of thermal pack 50 in positions relative to each other which are sufficiently close so as to block some or all possible axes across the material of continuous base layer 70 and/or carrier layer 72, which otherwise would have passed uninterrupted between heat cells 26, through thermal packs 50, or select regions thereof, to minimize or eliminate undesirable, uninterrupted fold lines, as described above.

Exothermic composition 74 may comprise any composition capable of providing heat. However, exothermic composition 74 preferably comprises a particulate mix of chemical compounds that undergo an oxidation reaction during use. Alternatively, exothermic composition 74 may also be formed into agglomerated granules, direct compacted into compaction articles such as granules, pellets, tablets, and/or slugs, and mixtures thereof. The mix of compounds typically comprises iron powder, carbon, a metal salt(s), and water. Mixtures of this type, which react when exposed to oxygen, provide heat for several hours.

Suitable sources for iron powder include cast iron powder, reduced iron powder, electrolytic iron powder, scrap iron powder, pig iron, wrought iron, various steels, iron alloys, and the like and treated varieties of these iron powders. There is no particular limitation to their purity, kind, etc. so long as it can be used to produce heat-generation with electrically conducting water and air. Typically, the iron powder comprises from about 30% to about 80% by weight, preferably from about 50% to about 70% by weight, of the particulate exothermic composition.

Active carbon prepared from coconut shell, wood, charcoal, coal, bone coal, etc. are useful, but those prepared from other raw materials such as animal products, natural gas, fats, oils and resins are also useful in the particulate exothermic composition of the present invention. There is no limitation to the kinds of active carbon used, however, the preferred active carbon has superior water holding capabilities and the different carbons may be blended to reduce cost. Therefore, mixtures of the above carbons are useful in the present invention as well. Typically, activated carbon, non-activated carbon, and mixtures thereof, comprises from about 3% to about 25%, preferably from about 8% to about 20%, most preferably from about 9% to about 15% by weight, of the particulate exothermic composition.

The metal salts useful in the particulate exothermic composition include sulfates such as ferric sulfate, potassium sulfate, sodium sulfate, manganese sulfate, magnesium sulfate; and chlorides such as cupric chloride, potassium chloride, sodium chloride, calcium chloride, manganese chloride, magnesium chloride and cuprous chloride. Also, carbonate salts, acetate salts, nitrates, nitrites and other salts can be used. In general, several suitable alkali, alkaline earth, and transition metal salts exist which can also be used, alone or in combination, to sustain the corrosive reaction of iron. The preferred metal salts are sodium chloride, cupric chloride, and mixtures thereof. Typically, the metal salt(s) comprises from about 0.5% to about 10% by weight, preferably from about 1.0% to about 5% by weight, of the particulate exothermic composition.

The water used in the particulate exothermic composition may be from any appropriate source. There is no particular limitation to its purity, kind, etc. Typically, water comprises from about 1% to about 40% by weight, preferably from about 10% to about 30% by weight, of the particulate exothermic composition.

Additional water-holding materials may also be added as appropriate. Useful additional water-holding materials include vermiculite, porous silicates, wood powder, wood flour, cotton cloth having a large amount of fluffs, short fibers of cotton, paper scrap, vegetable matter, super absorbent water-swellable or water-soluble polymers and resins, carboxymethylcellulose salts, and other porous materials having a large capillary function and hydrophilic property can be used. Typically, the additional water-holding materials comprise from about 0.1% to about 30% by weight, preferably from about 0.5% to about 20% by weight, most preferably from about 1% to about 10% by weight, of the particulate exothermic composition.

Other additional components include agglomeration aids such as gelatin, natural gums, cellulose derivatives, cellulose ethers and their derivatives, starch, modified starches, polyvinyl alcohols, polyvinylpyrrolidone, sodium alginates, polyols, glycols, corn syrup, sucrose syrup, sorbitol syrup and other polysaccharides and their derivatives, polyacrylamides, polyvinyloxoazolidone, and maltitol syrup; dry binders such as maltodextrin, sprayed lactose, co-crystallized sucrose and dextrin, modified dextrose, sorbitol, mannitol, microcrystalline cellulose, microfine cellulose, pre-gelatinized starch, dicalcium phosphate, and calcium carbonate; oxidation reaction enhancers such as elemental chromium, manganese, or copper, compounds comprising said elements, or mixtures thereof; hydrogen gas inhibitors such as inorganic or organic alkali compounds or alkali weak acid salts including sodium hydroxide, potassium hydroxide, sodium hydrogen carbonate, sodium carbonate, calcium hydroxide, calcium carbonate, and sodium propionate; fillers such as natural cellulosic fragments including wood dust, cotton linter, and cellulose, synthetic fibers in fragmentary form including polyester fibers, foamed synthetic resins such as foamed polystyrene and polyurethane, and inorganic compounds including silica powder, porous silica gel, sodium sulfate, barium sulfate, iron oxides, and alumina; and anti-caking agents such as tricalcium phosphate and sodium silicoaluminate. Such components also include thickeners such as cornstarch, potato starch, carboxymethylcellulose, and α-starch, and surfactants such as those included within the anionic, cationic, nonionic, zwitterionic, and amphoteric types. The preferred surfactant, if used however, is nonionic. Still other additional components which may be added to the particulate exothermic compositions of the present invention, as appropriate, include extending agents such as metasilicates, zirconium, and ceramics.

Preferably at least 50%, more preferably 70%, even more preferably 80% and most preferably 90% of all of the particles by weight of the particulate exothermic composition of the present invention have a mean particle size of less than 200 μm, preferably less than 150 μm.

The above-mentioned components of the composition are blended using conventional blending techniques. Suitable methods of blending these components are described in detail in U. S. Pat. No. 4,649,895 to Yasuki et al., issued Mar. 17, 1987 which is incorporated by reference herein in its entirety.

Alternatively to the above described particulate exothermic composition, the exothermic composition may be formed into agglomerated granules, direct compacted into compaction articles such as granules, pellets, tablets, and/or slugs, and mixtures thereof.

The exothermic composition of these agglomerated granules and/or compaction articles comprises iron powder, dry powdered carbonaceous material, an agglomeration aid, and a dry binder. Additionally, a metal salt, is added to the dry mix or subsequently as an aqueous/brine solution. Typically, the iron powder comprises from about 30% to about 80%, preferably from about 40% to about 70%, most preferably from about 50% to about 65% by weight; activated carbon, non-activated carbon, and mixtures thereof, comprises from about 3% to about 20%, preferably from about 5% to about 15%, most preferably from about 6% to about 12% by weight; the metal salt(s) comprises from about 0.5% to about 10%, preferably from about 1% to about 8%, most preferably from about 2% to about 6% by weight; the agglomeration aids comprise from about 0% to about 9%, preferably from about 0.5% to about 8%, more preferably from about 0.6% to about 6%, most preferably from about 0.7% to about 3% by weight; and the dry binder comprises from about 0% to about 35%, preferably from about 4% to about 30%, more preferably from about 7% to about 20%, most preferably from about 9% to about 15% by weight, of the agglomerated pre-compaction compositions of the present invention.

Heat cells comprising agglomerated granules are typically made using conventional blending techniques and agglomerated into granules.

Heat cells comprising compaction articles are preferably made by direct compaction of the dry ingredients into articles such as hard granules, pellets, tablets, and/or slugs. Suitable methods of making tablets and/or slugs are described in detail in Chapter 89, "Oral Solid Dosage Forms", *Reminton's Pharmaceutical Sciences,* 18th Edition, (1990), pp. 1634–1656, Alfonso R. Gennaro, ed., incorporated herein by reference in its entirety. Any conventional tableting machine and compression pressures, up to the maximum provided by the machine can be used.

The tablets/slugs can have any geometric shape consistent with the shape of the heat cell, e.g., disk, triangle, square, cube, rectangle, cylinder, ellipsoid and the like, all or none of which may contain a hole through the middle or other reservoir. A preferred shape of the tablet/slug comprises an ellipsoid. A more preferred shape of the tablet/slug, however, comprises a disk shaped geometry, having a concaved (whisper) configuration to the top and/or bottom of the tablet. A most preferred shape of the tablet/slug, comprises a disk shaped geometry, having a hole perpendicular to the upper and lower surface, and through the middle of the upper and lower surface, and body of the tablet.

The size of the compacted disk is limited only by the size of the punches and die available and/or used in the tableting machine, as well as the size of the heat cell pocket. However, the disk typically has a diameter of from about 0.2 cm to about 10 cm, preferably from about 0.5 cm to about 8 cm, more preferably from about 1 cm to about 5 cm, and most preferably from about 1.5 cm to about 3 cm and a height of from about 0.08 cm to about 1 cm, preferably from about 0.15 cm to about 0.8 cm, more preferably from about 0.2 cm to about 0.6 cm, and most preferably from about 0.2 cm to about 0.5 cm. Alternatively, the compacted disk having a geometric shape other than a disk shape may have a width at its widest point of from about 0.15 cm to about 20 cm, preferably from about 0.3 cm to about 10 cm, more preferably from about 0.5 cm to about 5 cm, most preferably from about 1 cm to about 3 cm, a height at its highest point of from about 0.08 cm to about 1 cm, preferably from about 0.15 cm to about 0.8 cm, more preferably from about 0.2 cm to about 0.6 cm, and most preferably from about 0.2 cm to about 0.5 cm, and a length at its longest point of from about 1.5 cm to about 20 cm, preferably from about 1 cm to about 15 cm, more preferably from about 1 cm to about 10 cm, most preferably from about 3 cm to about 5 cm. The hole or reservoir should be large enough to substantially hold the prescribed amount of water and/or the water-carrying material. Typically, the hole has a diameter of from about 0.1 cm to about 1 cm, preferably from about 0.2 cm to about 0.8 cm, and more preferably from about 0.2 cm to about 0.5 cm.

The compaction articles of the present invention are compressed to the hardest possible mechanical strength to withstand the shocks of handling in their manufacture, packing, shipping, and dispensing. The compaction articles are typically compressed to a density of greater than about 1 g/cm³, preferably from about 1 g/cm³ to about 3 g/cm³, more preferably from about 1.5 g/cm³ to about 3 g/cm³, and most preferably from about 2 g/cm³ to about 3 g/cm³.

Heat cells 26 comprising the above described components are typically formed by adding a fixed amount of a particulate exothermic composition or compaction article(s) 74 to a pocket or pockets made in continuous base layer 70.

Continuous cover layer 72 is placed over continuous base layer 70, sandwiching the particulate exothermic composition or compaction article(s) 74 between the base layer 70 and cover layer 72, which are then bonded together, preferably using a low heat, forming a unified, laminate structure. Preferably, each heat cell has a similar volume of heat generating material and has similar oxygen permeability means. However, the volume of the heat generating material, shape of the heat cell, and oxygen permeability may be different from heat cell to heat cell as long as the resulting cell temperatures generated are within accepted therapeutic and safety ranges for their intended use.

The ratio of fill volume to cell volume of the heat cells 26 is from about 0.7 to about 1.0, preferably from about 0.75 to about 1.0, more preferably from about 0.8 to about 1.0, even more preferably from about 0.85 to about 1.0, and most preferably from about 0.9 to about 1.0.

Oxygen permeability can be provided by selecting materials for the base layer 70 and/or cover layer 72 that have the specifically desired permeability properties. The desired permeability properties may be provided by microporous films or by films which have pores or holes formed therein. The formation of these holes/pores may be via extrusion cast/vacuum formation or by hot needle aperturing. The size of the apertures is preferably about 0.127 mm diameter, and there are preferably 25 to 40 apertures per heat cell 26. Another preferred method of making apertures is to pierce cell covering layer 72 with cold needles. Alternatively, apertures may be produced by a vacuum forming or a high pressure water jet forming process. Oxygen permeability may also be provided in the present invention by perforating at least one of the base layer 70 and cover layer 72 with aeration holes using, for example, an array of pins having tapered points and diameters of from about 0.2 mm to about 2 mm, preferably from about 0.4 mm to about 0.9 mm. The array of pins is patterned such that the base layer 70 and/or cover layer 72 are perforated by from about 10 to about 30 pins per square centimeter. Alternatively, after the base layer 70 and cover layer 72 have been bonded together, enclosing the exothermic composition 74 in the pocket between them, one side of the heat cells 26 may be perforated with aeration holes using, for example, at least one pin, preferably an array of from about 20 to about 60 pins having tapered points and diameters of from about 0.2 mm to about 2 mm, preferably from about 0.4 mm to about 0.9 mm. The pins are pressed through one side of the base layer 70 and/or cover layer 72 to a depth of from about 2% to about 100%, preferably from about 20% to about 100%, and more preferably from about 50% to about 100% into the exothermic composition 74. This hole configuration provides an oxygen diffusion into the heat cell 26 during oxidation of the particulate exothermic composition 74 of from about 0.01 cc $O_2$/min./5 cm² to about 15.0 cc $O_2$/min./5 cm² (at 21° C., 1 ATM), preferably from about 0.9 cc $O_2$/min./5 cm² to about 3 cc $O_2$/min./5 cm² (at 21° C., 1 ATM).

The velocity, duration, and temperature of the thermogenic oxidation reaction of the exothermic composition 74 can be controlled as desired by changing the area of contact with air, more specifically, by changing the oxygen diffusion/permeability.

The disposable thermal neck wraps of the present invention may optionally incorporate a component, such as a separate substrate layer or incorporated into at least one of the continuous layers, comprising active aromatic compounds, non-active aromatic compounds, pharmaceutical actives or other therapeutic agents, and mixtures thereof, to be delivered through the skin. Such active aromatic compounds include, but are not limited to, menthol, camphor, and eucalyptus. Such non-active aromatic compounds include, but are not limited to, benzaldehyde, citral, decanal, and aldehyde. Such pharmaceutical actives/therapeutic agents include, but are not limited to antibiotics, vitamins, antiviral agents, analgesics, anti-inflammatory agents, antipruritics, antipyretics, anesthetic agents, antifingals, antimicrobials, and mixtures thereof. The disposable thermal neck wraps may also comprise a separate substrate layer, or incorporated into at least one of the continuous layers, a self-adhesive component and/or a sweat-absorbing component.

The finished disposable thermal neck wraps are typically packaged in a secondary package. An air-impermeable package may be used to prevent an oxidation reaction from occurring until desired as described in U.S. Pat. No. 4,649,895, incorporated herein by reference in its entirety. Alternatively, other means may also be used to prevent an oxidation reaction from occurring before desired, such as air impermeable removable adhesive strips placed over the aeration holes in the heat cells such that, when the strips are removed, air is allowed to enter the heat cells, thus activating the oxidation reaction of the iron powder.

The present invention further comprises a method for treating acute, recurrent, and/or chronic upper back, neck, and/or shoulder pain, including muscular, skeletal, and/or referred upper back, neck, and/or shoulder pain, of a person suffering such pain by topically applying heat to the specific areas of the upper back, neck, and/or shoulders of a person suffering such pain. The method comprises maintaining a skin temperature to the upper back, neck, and/or shoulder of a person suffering such pain of from about 32° C. to about 50° C., preferably from about 32° C. to about 45° C., more preferably from about 32° C. to about 42° C., most preferably from about 32° C. to about 39° C., still most preferably from about 32° C. to about 37° C., preferably by applying the above described neck wraps to the upper back, neck, and/or shoulder of a person suffering such pain, for from about twenty seconds to about twenty-four hours, preferably from about twenty minutes to about twenty hours, more preferably from about four hours to about sixteen hours, most preferably from about eight hours to about twelve hours, wherein the maximum skin temperature and the length of time of maintaining the skin temperature at the maximum skin temperature may be appropriately selected by a person needing such treatment, such that the desired therapeutic benefits are achieved, without any adverse events, such as skin burns which may be incurred by using a high temperature for a long period of time.

Preferably the method comprises maintaining a sustained skin temperature to the upper back, neck, and/or shoulders of a person having acute, recurrent, and/or chronic upper back, neck, and/or shoulder pain, including muscular, skeletal, and/or referred upper back, neck, and/or shoulder pain, of from about 32° C. to about 43° C., preferably from about 32° C. to about 42° C., more preferably from about 32° C. to about 41° C., most preferably from about 32° C. to about 39° C., still most preferably from about 32° C. to about 37° C., for a time period of greater than about 1 hour, preferably greater than about 4 hours, more preferably greater than about 8 hours, even more preferably greater than about 16 hours, most preferably about 24 hours, to substantially relieve acute, recurrent, and/or chronic upper back, neck, and/or shoulder pain, including skeletal, muscular, and/or referred upper back, neck, and/or shoulder pain, of a person having such pain and to substantially prolong relief, for at least about 2 hours, preferably for at least about 8 hours, more preferably for at least about 16 hours, most preferably for at least about one day, still most preferably for at least about three days, from such pain, even after the heat source is removed from the upper back, neck, and/or shoulders of the user.

While particular embodiments of the present invention have been illustrated and described, it will be obvious to those skilled in the art that various changes and modifications may be made without departing from the spirit and scope of the invention, and it is intended to cover in the appended claims all such modifications that are within the scope of the invention.

What is claimed is:

1. A disposable thermal neck wrap comprising:
    a) at least one substantially U-shaped piece of flexible material, said piece of flexible material having a first arm portion, a second arm portion, and a central body portion therebetween, such that when said neck wrap is placed on a user, said central body portion is centered at said user's upper back and lower neck and said first and second arm portions lay across said user's shoulders toward said user's chest; and
    b) one or more thermal packs fixedly attached to said piece of flexible material, said thermal pack having a unified structure comprising at least one continuous layer of a semirigid material having a tensile strength of about 0.7 g/mm$^2$, or greater, and at least two-dimensional drape at a temperature of about 25° C., and wherein said material has a tensile strength, at a temperature of about 35° C. or greater, substantially less than said tensile strength of said material at about 25° C., and having a plurality of individual heat cells spaced apart and fixed within or to said unified structure of said thermal pack.

2. A disposable thermal neck wrap according to claim 1 wherein said at least one continuous layer comprises a tensile strength of about 0.85 g/mm$^2$, or greater, and at least two-dimensional drape at a temperature of about 25° C.

3. A disposable thermal neck wrap according to claim 2 wherein said at least one continuous layer comprises a tensile strength of about 1 g/mm$^2$, or greater, and at least two-dimensional drape at a temperature of about 25° C.

4. A disposable thermal neck wrap according to claim 1 wherein said at least one continuous layer comprises a material selected from the group consisting of polyethylene, polypropylene, nylon, polyester, polyvinyl chloride, polyvinylidene chloride, polyurethane, polystyrene, saponified ethylene-vinyl acetate copolymer, ethylene-vinyl acetate copolymer, natural rubber, reclaimed rubber, synthetic rubber, and mixtures thereof.

5. A disposable thermal neck wrap according to claim 4 wherein said at least one continuous layer comprises an extruded material selected from the group consisting of polyethylene, polypropylene, nylon, polyester, polyvinyl chloride, polyvinylidene chloride, polyurethane, polystyrene, saponified ethylene-vinyl acetate copolymer, and ethylene-vinyl acetate copolymer.

6. A disposable thermal neck wrap according to claim 5 wherein said at least one continuous layer comprises a coextruded material having a first side selected from the group consisting of polyethylene, polypropylene, nylon, polyester, polyvinyl chloride, polyvinylidene chloride, polyurethane, and polystyrene, and a second side selected from the group consisting of saponified ethylene-vinyl acetate copolymer and ethylene-vinyl acetate copolymer.

7. A disposable thermal neck wrap according to claim 6 wherein said at least one continuous layer comprises a coextruded material having a first side of polypropylene and a second side of ethylene-vinyl acetate copolymer.

8. A disposable thermal neck wrap according to claim 7 wherein said at least one continuous layer comprises a coextruded material having a first side of polypropylene and a second side of ethylene vinyl acetate copolymer, wherein said polypropylene comprises from about 10% to about 90% of the total thickness of said material.

9. A disposable thermal neck wrap according to claim 8 wherein said at least one continuous layer comprises a coextruded material having a first side of polypropylene and a second side of ethylene vinyl acetate copolymer, wherein said polypropylene comprises from about 40% to about 60% of the total thickness of the material.

10. A disposable thermal neck wrap according to claim 1 further comprising a positioning means attached to distal ends of at least one of said first and second arm portions.

11. A disposable thermal neck wrap according to claim 10 wherein said positioning means is selected from the group consisting of one or more adhesive patches and hook and loop fastening system.

12. A disposable thermal neck wrap according to claim 1 wherein one or more of said heat cells of said thermal packs are located within each of said arms.

13. A disposable thermal neck wrap according to claim 1 wherein said heat cells comprise a shape selected from the group consisting of a disk, triangle, pyramid, cone, sphere, square, cube, rectangle, rectangular parallelepiped, cylinder, and ellipsoid, said disk having a diameter of from about 1 cm to about 5 cm and a height of from greater than about 0.2 cm to about 1 cm and said triangle, pyramid, cone, sphere, square, cube, rectangle, rectangular parallelepiped, cylinder, and ellipsoid having a width at its widest point of from about 0.5 cm to about 5 cm and a height at its highest point of from greater than about 0.2 cm to about 1 cm and a length at its longest point of from about 1.5 cm to about 10 cm, and wherein said heat cells, when filled with an exothermic composition, have a fill volume to cell volume ratio of from about 0.7 to about 1.0.

14. A disposable thermal neck wrap according to claim 13 wherein said exothermic composition comprises:
    a.) from about 30% to about 80% by weight, iron powder;
    b.) from about 3% to about 25% by weight, carbonaceous material selected from the group consisting of activated carbon, non-activated carbon, and mixtures thereof;
    c.) from about 0.5% to about 10% by weight, metal salt; and
    d.) from about 1% to about 40% by weight, water.

15. A disposable thermal neck wrap according to claim 14 wherein said exothermic composition comprises from about 0.1% to about 30% by weight, of additional water-holding material.

16. A disposable thermal neck wrap according to claim 13 wherein said exothermic composition comprises:
    a.) from about 30% to about 80% by weight, of iron powder;
    b.) from about 3% to about 20% by weight, of carbonaceous material selected from the group consisting of activated carbon, non-activated carbon, and mixtures thereof;

c.) from about 0% to about 9% by weight, of an agglomeration aid selected from the group consisting of corn syrup, maltitol syrup, crystallizing sorbitol syrup, amorphous sorbitol syrup, and mixtures thereof; and d.) from about 0% to about 35% by weight, of a dry binder selected from the group consisting of microcrystalline cellulose, maltodextrin, sprayed lactose, co-crystallized sucrose and dextrin, modified dextrose, mannitol, microfine cellulose, pre-gelatinized starch, dicalcium phosphate, calcium carbonate, and mixtures thereof; wherein from about 0.5% to about 10% by weight, of a metal salt selected from the group consisting of alkali metal salts, alkaline earth metal salts, transitional metal salts, and mixtures thereof is added to said composition as part of the dry mix or subsequently in an aqueous solution as brine, and further wherein said exothermic composition comprises a physical form selected from the group consisting of dry agglomerated granules, direct compaction articles, and mixtures thereof, wherein said direct compaction articles are selected from the group consisting of granules, pellets, tablets, slugs, and mixtures thereof, and wherein said tablets and slugs comprise a geometric shape selected from the group consisting of disk, triangle, square, cube, rectangle, cylinder, and ellipsoid, said disk having a diameter of from about 1 cm to about 5 cm and a height of from about 0.08 cm to about 1 cm and said triangle, square, cube, rectangle, cylinder, and ellipsoid having a width at its widest point of from about 0.5 cm to about 5 cm and a height at its highest point of from about 0.08 cm to about 1 cm and a length at its longest point of from about 1 cm to about 10 cm.

17. A disposable thermal neck wrap according to claim 16 wherein said exothermic composition further comprises from about 0.5% to about 10% by weight, of additional water-holding materials selected from the group consisting of acrylic acid salt starch co-polymer, isobutylene maleic anhydride co-polymer, vermiculite, carboxymethylcellulose, and mixtures thereof.

18. A disposable thermal neck wrap according to claim 16 wherein said dry binder comprises from about 4% to about 30% by weight, of microcrystalline cellulose.

19. A disposable thermal neck wrap according to claim 16 wherein said tablets comprise a geometric shape selected from the group consisting of a disk shape having a hole passing perpendicular to and through the middle of the top and bottom surfaces and a disk shape wherein the top and bottom surfaces are concaved forming a reservoir conducive to holding a liquid.

20. A disposable thermal neck wrap according to claim 16 wherein said direct compaction articles comprise a density of greater than about 1 g/cm$^3$.

21. A disposable thermal neck wrap according to claim 1 further comprising additional components selected from the group consisting of active aromatic compounds, non-active aromatic compounds, pharmaceutical actives, and mixtures thereof.

22. A disposable thermal neck wrap comprising at least one thermal pack having a unified structure comprising at least one continuous layer of material and a plurality of individual heat cells, said heat cells are placed into positions fixed within or to said unified structure of said thermal pack which are sufficiently close and relative to each other, so as to block some or all possible axes across said at least one continuous layer, which otherwise would have passed uninterrupted between said heat cells, through said thermal pack, or select regions thereof.

23. A disposable thermal neck wrap according to claim 22 wherein at least one of said heat cells of four adjacent said heat cells, whose centers form a quadrilateral pattern, blocks one or more of said axes that could otherwise form at least one fold line tangential to the edges of one or more pairings of the remaining said heat cells in the quadrilateral pattern.

24. A disposable thermal neck wrap according to claim 23 wherein the spacing between said at least one of said heat cells and each of said heat cells of said one or more pairings of said remaining heat cells in said quadrilateral pattern is the same or less than the spacing obtained by dividing the measurement of the smallest diameter of the smallest diameter heat cell of said heat cells within said quadrilateral pattern by 2 and multiplying the result by 0.75.

25. A disposable thermal neck wrap according to claim 22 wherein at least one of said heat cells of three adjacent said heat cells, whose centers form a triangular pattern, blocks one or more of said axes that could otherwise form at least one fold line tangential to the edges of the remaining pair of said heat cells in the triangular pattern formed by said three heat cells.

26. A disposable thermal neck wrap according to claim 25 wherein the spacing between said at least one of said heat cells and each of said heat cells of said remaining pair of said heat cells in said triangular pattern is the same or less than the spacing obtained by dividing the measurement of the smallest diameter of the smallest diameter heat cell of said heat cells within said triangular pattern by 2 and multiplying the result by 0.3.

27. A disposable thermal neck wrap according to claim 22 wherein said at least one continuous layer comprises a semirigid material having a tensile strength of about 0.7 g/mm$^2$, or greater, and at least two-dimensional drape at a temperature of about 25° C., and wherein said material has a tensile strength, at a temperature of about 35° C. or greater, substantially less than said tensile strength of said material at about 25° C.

28. A disposable thermal neck wrap according to claim 27 wherein said at least one continuous layer comprises a material selected from the group consisting of polyethylene, polypropylene, nylon, polyester, polyvinyl chloride, polyvinylidene chloride, polyurethane, polystyrene, saponified ethylene-vinyl acetate copolymer, ethylene-vinyl acetate copolymer, natural rubber, reclaimed rubber, synthetic rubber, and mixtures thereof.

29. A disposable thermal neck wrap according to claim 28 wherein said at least one continuous layer comprises a coextruded material having a first side selected from the group consisting of polyethylene, polypropylene, nylon, polyester, polyvinyl chloride, polyvinylidene chloride, polyurethane, and polystyrene, and a second side selected from the group consisting of saponified ethylene-vinyl acetate copolymer and ethylene-vinyl acetate copolymer.

30. A disposable thermal neck wrap according to claim 29 wherein said at least one continuous layer comprises a coextruded material having a first side of polypropylene and a second side of ethylene-vinyl acetate copolymer.

31. A disposable thermal neck wrap according to claim 22 further comprising a positioning means attached to distal ends of at least one of said first and second arm portions.

32. A disposable thermal neck wrap according to claim 31 wherein said positioning means is selected from the group consisting of one or more adhesive patches and hook and loop fastening system.

33. A disposable thermal neck wrap according to claim 22 wherein one or more of said heat cells of said thermal packs are located within each of said arms.

34. A disposable thermal neck wrap according to claim 22 wherein said heat cells comprise a shape selected from the group consisting of a disk, triangle, pyramid, cone, sphere, square, cube, rectangle, rectangular parallelepiped, cylinder, and ellipsoid, said disk having a diameter of from about 1 cm to about 5 cm and a height of from greater than about 0.2 cm to about 1 cm, and said triangle, pyramid, cone, sphere, square, cube, rectangle, rectangular parallelepiped, cylinder, and ellipsoid having a width at its widest point of from about 0.5 cm to about 5 cm and a height at its highest point of from greater than about 0.2 cm to about 1 cm and a length at its longest point of from about 1.5 cm to about 10 cm, and wherein said heat cells, when filled with an exothermic composition, have a fill volume to cell volume ratio of from about 0.7 to about 1.0.

35. A disposable thermal neck wrap according to claim 34 wherein said exothermic composition comprises:
   a.) from about 30% to about 80% by weight, iron powder;
   b.) from about 3% to about 25% by weight, carbonaceous material selected from the group consisting of activated carbon, non-activated carbon, and mixtures thereof;
   c.) from about 0.5% to about 10% by weight, metal salt; and
   d.) from about 1% to about 40% by weight, water.

36. A disposable thermal neck wrap according to claim 35 wherein said exothermic composition farther comprises from about 0.1% to about 30% by weight, of additional water-holding material.

37. A disposable thermal neck wrap according to claim 34 wherein said exothermic composition comprises:
   a.) from about 30% to about 80% by weight, of iron powder;
   b.) from about 3% to about 20% by weight, of carbonaceous material selected from the group consisting of activated carbon, non-activated carbon, and mixtures thereof;
   c.) from about 0% to about 9% by weight, of an agglomeration aid selected from the group consisting of corn syrup, maltitol syrup, crystallizing sorbitol syrup, amorphous sorbitol syrup, and mixtures thereof; and
   d.) from about 0% to about 35% by weight, of a dry binder selected from the group consisting of microcrystalline cellulose, maltodextrin, sprayed lactose, co-crystallized sucrose and dextrin, modified dextrose, mannitol, microfine cellulose, pre-gelatinized starch, dicalcium phosphate, calcium carbonate, and mixtures thereof;
wherein from about 0.5% to about 10% by weight, of a metal salt selected from the group consisting of alkali metal salts, alkaline earth metal salts, transitional metal salts, and mixtures thereof is added to said composition as part of the dry mix or subsequently in an aqueous solution as brine, and wherein further said exothermic composition comprises a physical form selected from the group consisting of dry agglomerated granules, direct compaction articles, and mixtures thereof, wherein said direct compaction articles are selected from the group consisting of granules, pellets, tablets, slugs, and mixtures thereof, and wherein said tablets and slugs comprise a geometric shape selected from the group consisting of disk, triangle, square, cube, rectangle, cylinder, and ellipsoid, said disk having a diameter of from about 1 cm to about 5 cm and a height of from about 0.08 cm to about 1 cm and said triangle, square, cube, rectangle, cylinder, and ellipsoid having a width at its widest point of from about 0.5 cm to about 5 cm and a height at its highest point of from about 0.08 cm to about 1 cm and a length at its longest point of from about 1 cm to about 10 cm.

38. A disposable thermal neck wrap according to claim 37 wherein said exothermic composition further comprises from about 0.5% to about 10% by weight, of additional water-holding materials selected from the group consisting of acrylic acid salt starch co-polymer, isobutylene maleic anhydride co-polymer, vermiculite, carboxymethylcellulose, and mixtures thereof.

39. A disposable thermal neck wrap according to claim 37 wherein said dry binder comprises from about 4% to about 30% by weight, of microcrystalline cellulose.

40. A disposable thermal neck wrap according to claim 37 wherein said tablets comprise a geometric shape selected from the group consisting of a disk shape having a hole passing perpendicular to and through the middle of the top and bottom surfaces and a disk shape wherein said top and bottom surfaces are concaved forming a reservoir conducive to holding a liquid.

41. A disposable thermal neck wrap according to claim 37 wherein said direct compaction articles comprise a density of greater than about 1 g/cm$^3$.

42. A disposable thermal neck wrap according to claim 22 further comprising additional components selected from the group consisting of active aromatic compounds, non-active aromatic compounds, pharmaceutical actives, and mixtures thereof.

43. A method of treating upper back, neck, and shoulder pain, selected from the group consisting of acute muscular, acute skeletal, acute referred, recurrent muscular, recurrent skeletal, recurrent referred, chronic muscular, chronic skeletal, and chronic referred upper back, neck, and shoulder pain, by applying a disposable thermal neck wrap of claim 1 to the upper back, neck, and shoulders of a person needing such treatment, to maintain a skin temperature to the back of from about 32° C. to about 50° C. for a time period of from about twenty seconds to about twenty-four hours, wherein said skin temperature and said period of time of maintaining said skin temperature is appropriately selected by said person needing such treatment, to substantially relieve said pain without adverse events.

44. A method of treating upper back, neck, and shoulder pain according to claim 43 wherein said skin temperature is maintained from about 32° C. to about 39° C.

45. A method of treating upper back, neck, and shoulder pain according to claim 43 wherein said skin temperature is maintained at a temperature of from about 32° C. to about 43° C. for a time period of greater than about 1 hour, wherein said relief of said pain is substantially prolonged for at least about 2 hours after removal of said heat from the upper back, neck, and shoulders of said person needing such treatment.

46. A method of treating upper back, neck, and shoulder pain according to claim 45 wherein said skin temperature is maintained at a temperature of from about 32° C. to about 41° C. for a time period of greater than about 4 hours, wherein said relief of said pain is substantially prolonged for at least about 1 day after removal of said heat from the upper back, neck, and shoulders of said person needing such treatment.

47. A method of treating upper back, neck, and shoulder pain, selected from the group consisting of acute muscular, acute skeletal, acute referred, recurrent muscular, recurrent skeletal, recurrent referred, chronic muscular, chronic skeletal, and chronic referred upper back, neck, and shoulder pain, by applying a disposable thermal neck wrap of claim 22 to the upper back, neck, and shoulders of a person needing such treatment, to maintain a skin temperature to the back of from about 32° C. to about 50° C. for a time period of from about twenty seconds to about twenty-four hours, wherein said skin temperature and said period of time of maintaining said skin temperature is appropriately selected by said person needing such treatment, to substantially relieve said pain without adverse events.

48. A method of treating upper back, neck, and shoulder pain according to claim 47 wherein said skin temperature is maintained from about 32° C. to about 39° C.

49. A method of treating upper back, neck, and shoulder pain according to claim 47 wherein said skin temperature is maintained at a temperature of from about 32° C. to about 43° C. for a time period of greater than about 1 hour, wherein said relief of said pain is substantially prolonged for at least about 2 hours after removal of said heat from the upper back, neck, and shoulders of said person needing such treatment.

50. A method of treating upper back, neck, and shoulder pain according to claim 49 wherein said skin temperature is maintained at a temperature of from about 32° C. to about 41° C. for a time period of greater than about 4 hours, wherein said relief of said pain is substantially prolonged for at least about 1 day after removal of said heat from the upper back, neck, and shoulders of said person needing such treatment.

* * * * *